(12) United States Patent
Vondran et al.

(10) Patent No.: US 11,930,831 B2
(45) Date of Patent: *Mar. 19, 2024

(54) COMPOSITION AND METHOD FOR REDUCING OR TREATING ORAL INFLAMMATION

(71) Applicant: Hill's Pet Nutrition, Inc., Topeka, KS (US)

(72) Inventors: Jodi Vondran, Wamego, KS (US);
Dennis Jewell, Lawrence, KS (US);
Kiran Panickar, Lawrence, KS (US);
Dale Scherl, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1067 days.

This patent is subject to a terminal disclaimer.

(21) Appl. No.: 16/700,204

(22) Filed: Dec. 2, 2019

(65) Prior Publication Data

US 2020/0100526 A1 Apr. 2, 2020

Related U.S. Application Data

(63) Continuation of application No. 15/533,185, filed as application No. PCT/US2014/070804 on Dec. 17, 2014, now Pat. No. 10,524,488.

(51) Int. Cl.
| | | |
|---|---|---|
| *A61K 9/00* | (2006.01) | |
| *A23K 10/30* | (2016.01) | |
| *A23K 40/25* | (2016.01) | |
| *A23K 50/40* | (2016.01) | |
| *A61K 9/20* | (2006.01) | |
| *A61K 31/12* | (2006.01) | |
| *A61K 36/185* | (2006.01) | |
| *A61K 36/82* | (2006.01) | |
| *A61K 36/9066* | (2006.01) | |
| *A61P 1/02* | (2006.01) | |
| *A61P 29/00* | (2006.01) | |

(52) U.S. Cl.
CPC .............. *A23K 10/30* (2016.05); *A23K 40/25* (2016.05); *A23K 50/40* (2016.05); *A61K 9/0056* (2013.01); *A61K 9/2072* (2013.01); *A61K 31/12* (2013.01); *A61K 36/185* (2013.01); *A61K 36/82* (2013.01); *A61K 36/9066* (2013.01)

(58) Field of Classification Search
CPC ........ A23K 10/30; A23K 40/25; A23K 50/40; A61K 2300/00; A61K 31/12; A61K 36/185; A61K 36/82; A61K 36/9066; A61K 9/0056; A61K 9/2072; A61P 1/02; A61P 29/00
See application file for complete search history.

(56) References Cited

U.S. PATENT DOCUMENTS

| | | | |
|---|---|---|---|
| 8,168,161 B2 | 5/2012 | Scherl et al. | |
| 8,679,564 B2 | 3/2014 | Suttle et al. | |
| 2004/0234579 A1 | 11/2004 | Finke | |
| 2008/0085338 A1* | 4/2008 | Krammer | A23K 40/30 |
| | | | 426/546 |
| 2009/0239943 A1 | 9/2009 | Sarkar | |
| 2012/0201914 A1 | 8/2012 | Huang et al. | |
| 2013/0122164 A1 | 5/2013 | Montelongo et al. | |
| 2014/0314819 A1 | 10/2014 | Scherl | |

FOREIGN PATENT DOCUMENTS

| | | | |
|---|---|---|---|
| CN | 101119634 | 2/2008 | |
| CN | 103054010 | 4/2013 | |
| EP | 0 337 571 A1 * | 10/1989 | ............... A23K 1/18 |
| GB | 2402377 | 12/2004 | |
| JP | H6-62763 | 3/1994 | |
| JP | 2010158200 | 7/2010 | |
| WO | 2006/069241 | 6/2006 | |
| WO | 2006/069662 | 7/2006 | |
| WO | 2008/057136 | 5/2008 | |
| WO | 2009/031023 | 3/2009 | |
| WO | 2012/018913 | 2/2012 | |
| WO | 2012/088519 | 6/2012 | |
| WO | 2012/103056 | 8/2012 | |
| WO | 2013/089842 | 6/2013 | |

OTHER PUBLICATIONS

International Search Report and Written Opinion of the International Searching Authority in International Application No. PCT/US2014/070804, dated Jul. 29, 2015.
Kiefer' Dale; "Report: Disease Prevention Begins in the Mouth"; Life Extension Magazine; 16 pages (pdf); published Sep. 2008.
LoveMeow; ("What's better for your Cat, Dry Kibble or Moist, Wet Food"; published online Jun. 13, 2009) www.lovemeow.com/whats-better-for-your-cat-dry-kibble-or-moist-wet-food-1607943436.html; pdf attached.
Nagpal et al.; "Role of curcumin in systemic and oral health: An overview"; J Nat Sci Biol Med. Jan.-Jun. 2013; 4(1): 3-7.

* cited by examiner

*Primary Examiner* — Jeffrey T. Palenik

(57) ABSTRACT

The current invention relates to animal food kibbles having a primarily disc shape and including botanicals such as curcumin. The current invention also relates to methods to reduce oral inflammation in an animal by feeding the animal with the food kibbles. The disc-shaped food kibbles induce a reduction of oral inflammation in the animal compared to control food kibbles having a different shape.

19 Claims, No Drawings

COMPOSITION AND METHOD FOR REDUCING OR TREATING ORAL INFLAMMATION

BACKGROUND

Dried animal or pet food products such as food kibbles are widely marketed for pets such as cats and dogs. In general, pet food kibbles have a relatively low moisture content and come with various shapes, sizes and colors. The food kibbles also provide nutrition for the pets by including a variety of ingredients. Extrusion cooking processes are usually used for the production of pet food kibbles and these processes have been a significant factor in the significant growth of the pet food kibble market.

Although pet food kibbles are generally well accepted by the animal, it is always desirable to improve the palatability of pet food. It is further desirable that the pet food kibbles would provide therapeutic or relieving effects for pet illness or discomfort. For example, oral inflammation, such as but not limited to gingivitis, may cause irritation and discomfort in the pet and may also result in long-term and severe complications. Thus, there is a need to develop pet food kibbles that are highly palatable and provide health benefits to the pet.

BRIEF SUMMARY

The current invention relates to method of reducing or treating oral inflammation in an animal, comprising feeding the animal primarily disc-shaped food kibbles comprising one or more botanicals, wherein a reduction of oral inflammation is achieved in the animal after or during ingestion of the disc-shaped kibbles.

The current invention also relates to a food kibble comprising one or more botanicals, wherein the food kibble has primarily a disc shape and reduces oral inflammation in an animal when the animal ingests the food kibble.

The current invention also relates to a method for making food kibbles containing one or more botanicals, the method comprising (a) preconditioning by mixing wet and dry ingredients at elevated temperature to form a kibble dough, (b) extruding the kibble dough at a high temperature and pressure through an extruder configured to form food kibbles having primarily a disc shape, (c) drying the extruded disc-shaped food kibbles, and (d) enrobing the dried disc-shaped food kibbles with topical liquid and/or dry ingredients, wherein the one or more botanicals are applied at (a) and/or (d) in an amount effective to reduce oral inflammation in an animal when the animal ingests the food kibbles.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of certain embodiment(s) is merely exemplary in nature and is in no way intended to limit the invention, its application, or uses. As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "kibble" or "food kibble" refers to a particulate pellet like component of animal feeds, such as dog and cat feeds. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term "kibble" or "food kibble" is used, it can refer to an uncoated kibble or a coated kibble.

As used herein, the term "extrude" or "extrusion" refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble in a desired shape, e.g. disc shape. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As used herein, unless otherwise stated for a particular parameter, the term "about" refers to a range that encompasses an industry-acceptable range for inherent variability in analyses or process controls, including sampling error. Consistent with the Model Guidance of AAFCO, inherent variability is not meant to encompass variation associated with sloppy work or deficient procedures, but, rather, to address the inherent variation associated even with good practices and techniques.

As used herein, the term "animal" means any non-human organism belonging to the kingdom Animalia. The term "pet" means a domestic animal including but not limited to domestic dogs, cats, horses, cows, ferrets, rabbits, pigs, rats, mice, gerbils, hamsters, horses, minks, and the like. Domestic dogs and cats are particular examples of pets. It will be appreciated by one of skill in the art that some pets have different nutritional needs and some pets have similar nutritional needs. Further, nutritional needs are not necessarily consistent with phylogenetic or other non-nutritional classifications.

As used here, the term "botanicals" refer to food or dietary supplements extracted or derived from a plant or herbal source that can provide health benefits and/or treat/prevent diseases. Some exemplary botanicals may include components such as but not limited to curcumin, green tea, pomegranate, chamomile extracts, rosemary, aloe, nettle, centella asiatica, Ginkgo Biloba, betula, witch hazel, grape skin extract, grape seed extract, grapefruit extract, grapefruit seed extract, bilberry extract, blueberry extract, soy isoflavones, black cohosh, St. John's wort, echinacea, and chamomile. The botanicals may be extracted or derived from sources such as but not limited to acai, aloe vera, Asian ginseng, astragalus, bilberry, bitter orange, black cohosh, butterbury, cat's claw, chamomile, chasteberry, cinnamon, cranberry, candelion, echinacea, ephedra, European elder, European mistletoe, evening primrose oil, fenugreek, feverfew, flaxseed and flaxseed oil, garlic, ginger, ginkgo, goldenseal, grape seed extract, green tea, hawthorn, hoodia, horse chestnut, kava, lavender, licorice root, milk thistle, noni, passionflower, peppermint oil, red clover, sage, saw palmetto soy, St. John's wort, tea tree oil, thunder god vine, turmeric, valerian, and yohimbe, and other sources listed in nlm.nih.gov/medlineplus/druginfo/herb_All.html.

As used herein, the terms "disc shape" or "disc-shaped kibble" refer to food kibble shapes that have an essentially flat circular structure. A disc shape may be viewed as a compressed cylinder structure with a minimized height or thickness and round top and bottom views. A disc-shaped kibble may have a thickness measured from the top round surface to the bottom round surface and a diameter measured across the top/bottom round surface. In general, it is understood that a disc shape is shorter than it is wide. In some embodiments, a disc-shaped kibble may have a thickness to diameter ratio of about or less than about 1:1.1, 1:1.2, 1:1.3, 1:1.4, 1:1.5, 1:1.6, 1:1.7, 1:1.8, 1:1.9, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:16, 1:17, 1:18, 1:19, or 1:20. In one embodiment, the disc-shaped kibble has a thickness to diameter ratio of about 1:2.

As used herein, the phrases "primarily disc-shaped" or "having a primarily disc shape" or "essentially disc-shaped" refer to the shape of the food kibble where there may be minor distortions, modifications, additions, or reductions to the disc shape. For example, the food kibble may have apertures, holes or cavities through or on the top surface and/or the bottom surface; the food kibble may have bumps, projections, or apophysis on the top, bottom and/or side surfaces of the food kibble; the top and/or bottom surfaces may or may not be a perfect circular shape; the disc shape may be twisted, compressed or bent and the food kibble may not be of uniform thickness. A person skilled in the art would be able to discern whether a food kibble has a primarily disc shape.

The food kibble may be any size. For example, a primarily disc-shaped food kibble may have a thickness that is about or less than about 25 mm, 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4.75 mm, 4.5 mm, 4.25 mm, 4 mm, 3.75 mm, 3.5 mm, 3.25 mm, 3 mm, 2.75 mm, 2.5 mm, 2.25 mm, 2 mm, 1.75 mm, 1.5 mm, 1.25 mm, 1 mm, 0.75 mm, or 0.5 mm. In some embodiments, the primarily disc-shaped food kibble may have thickness of between about 1-20 mm, 1-19 mm, 1-18 mm, 1-17 mm, 1-16 mm, 1-15 mm, 1-14 mm, 1-13 mm, 1-12 mm, 1-11 mm, 1-10 mm, 1-9 mm, 1-8 mm, 1-7 mm, 1-6 mm, 1-5 mm, 1-4 mm, 1-3 mm, 1-2 mm, 2-20 mm, 2-19 mm, 2-18 mm, 2-17 mm, 2-16 mm, 2-15 mm, 2-14 mm, 2-13 mm, 2-12 mm, 2-11 mm, 2-10 mm, 2-9 mm, 2-8 mm, 2-7 mm, 2-6 mm, 2-5 mm, 2-4 mm, 2-3 mm, 2.5-20 mm, 2.5-19 mm, 2.5-18 mm, 2.5-17 mm, 2.5-16 mm, 2.5-15 mm, 2.5-14 mm, 2.5-13 mm, 2.5-12 mm, 2.5-11 mm, 2.5-10 mm, 2.5-9 mm, 2.5-8 mm, 2.5-7 mm, 2.5-6 mm, 2.5-5 mm, 2.5-4 mm, or 2.5-3 mm. In some embodiments, a disc-shaped food kibble may have a top/bottom surface diameter that is about or less than about 25 mm, 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4.75 mm, 4.5 mm, 4.25 mm, 4 mm, 3.75 mm, 3.5 mm, 3.25 mm, 3 mm, 2.75 mm, 2.5 mm, 2.25 mm, 2 mm, 1.75 mm, 1.5 mm, 1.25 mm, 1 mm, 0.75 mm, or 0.5 mm. In some embodiments, a disc-shaped food kibble may have a top/bottom surface diameter that is between about 2-20 mm, 2-19 mm, 2-18 mm, 2-17 mm, 2-16 mm, 2-15 mm, 2-14 mm, 2-13 mm, 2-12 mm, 2-11 mm, 2-10 mm, 2-9 mm, 2-8 mm, 2-7 mm, 2-6 mm, 2-5 mm, 2-4 mm, 2-3 mm, 5-20 mm, 5-19 mm, 5-18 mm, 5-17 mm, 5-16 mm, 5-15 mm, 5-14 mm, 5-13 mm, 5-12 mm, 5-11 mm, 5-10 mm, 5-9 mm, 5-8 mm, 5-7 mm, or 5-6 mm.

As used herein, the term "inflammation" refers to reactions redness, swelling, pain, tenderness, heat, or disturbed function of an area of an animal's body, especially as a reaction of tissues to injurious agents such as but not limited to bacteria. As used herein, inflammation may or may not refer to clinical inflammation and does not necessarily imply a specific biological response or imply the inducement of a specific type of effector cell in any process in the animal. In one embodiment, however, the term "inflammation" may include the "inflammation reaction" in which an animal's inflammatory cells, such as but not limited to myeloid leukocytes, lymphocytes, and gingival fibroblasts release inflammatory materials in a local environment. As used herein, the inflammation can be acute or chronic, and the methods and diets disclosed herein can be used to treat and/or prevent acute or chronic inflammation.

As used herein, the term "oral inflammation" refers to inflammation occurring in the oral cavity of an animal. For example, oral inflammation may include but not limited to gingivitis, periodontitis, swelling, redness and/or ulcers that affects any part of the mouth, such as but not limited to gums, tongue, throat, tonsils, uvula, hard palate, soft palate, and inner and outer lips.

The oral inflammation of an animal, such as but not limited to a cat, may be measured with a graded oral inflammation score. The graded oral inflammation score is generated by measuring the severity of oral inflammation (e.g. redness and swelling) based on a scoring system of 0=None, 1=Mild, 2=Moderate, to 3=Severe. The graded oral inflammation score measurement is known in the art and similar methods have been disclosed in references such as but not limited to Logan E. et al. *J. Vet. Dent.* 19(1):15-18 (2002), which is incorporated herein by reference. The final score reflects oral inflammation of the gums and the entire mouth of each animal. The graded oral inflammation score provide a quantifiable measurement for the level of oral inflammation of the animal, allowing assessment of the effectiveness of diet or drug to reduce oral inflammation. In some embodiments, the graded oral inflammation score may be assessed by a single qualified dental technician who was blinded to the study.

The current invention also relates to compositions comprising a food kibble comprising one or more botanicals, wherein the food kibble has primarily a disc shape and reduces oral inflammation in an animal when the animal ingests the food kibble.

In addition, the current invention also relates to a method of reducing or treating oral inflammation in an animal, comprising feeding the animal primarily disc-shaped food kibbles comprising one or more botanicals, wherein a reduction of oral inflammation is achieved in the animal after or during ingestion of the disc-shaped kibbles.

In some embodiments, the animal is a pet. In specific embodiments, the animal is a cat, such as but not limited to a domesticated house cat. In more specific embodiments, the animal is a kitten. Here a "kitten" refers to a juvenile (non-adult) domesticated cat. In a specific embodiment, the kitten has been weaned or is being weaned.

The food kibbles in the composition of the present invention comprise one or more botanicals. In some embodiments, the one or more botanicals may be less than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99% or 100% of the total kibble by weight. In some embodiments, the one or more botanicals may be more than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99% or 99.9% of the total kibble by weight. In some embodiments, the one or more botanicals may be about 0.01%, 0.05%, 0.1%, 0.15%, 0.2%, 0.25%, 0.3%, 0.35%, 0.4%, 0.45%, or 0.5% of the total kibble by weight. In one embodiment, the one or more botanicals may be about 0.1% of the total kibble by weight.

In one embodiment, the one or more botanicals comprise curcumin. In some embodiments, the curcumin may be less than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99% or 100% of the total botanicals by weight. In some embodiments, the curcumin may be more than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99% or 99.9% of the total botanicals by weight. In some embodiments, the curcumin may be less than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, or 50% of the total food kibble by weight. In some embodiments, the curcumin may be more than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, or 50% of the total food kibble by weight. In some embodiments, the curcumin is about 0.01%, 0.05%, 0.1%, 0.15%, 0.2%, 0.25%, 0.3%, 0.35%, 0.4%, 0.45% or 0.5% of the total food kibble by weight. In one embodiment, the curcumin is about 0.1% of the total food kibble by weight.

The food kibbles may comprise one or more botanicals such as but not limited to green tea and pomegranate. In one embodiment, the food kibble comprises curcumin but not green tea or pomegranate. In one embodiment, the food kibble comprises curcumin and green tea, but not pomegranate. In one embodiment, the food kibble comprises curcumin and pomegranate, but not green tea. In one embodiment, the food kibble comprises green tea, but not curcumin or pomegranate. In one embodiment, the food kibble comprises green tea and pomegranate, but not curcumin. In one embodiment, the food kibble comprises pomegranate, but not green tea or curcumin. In one embodiment, the food kibble comprises pomegranate, green tea and curcumin. If present, the green tea and/or pomegranate may be less than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99% or 100% of the total botanicals by weight. If present, the green tea and/or pomegranate may be more than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99% or 99.9% of the total botanicals by weight. If present, the green tea and/or pomegranate may be less than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, or 50% of the total kibble by weight. If present, the green tea and/or pomegranate may be more than about 0.001%, 0.01%, 0.1%, 0.5%, 1%, 2%, 3%, 4%, 5%, 6%, 7%, 8%, 9%, 10%, 11%, 12%, 13%, 14%, 15%, 20%, 25%, 30%, 35%, 40%, 45%, or 50% of the total food kibble by weight.

Food kibbles comprising different botanicals may be combined or mixed in a single diet. For example, in a diet of food kibbles, only some of the kibbles contain curcumin. In one embodiment, the curcumin-containing kibbles may be more than about 0.1%, 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In another embodiment, the curcumin-containing kibbles may be less than about 0.1%, 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In another diet of food kibbles, only some of the kibbles contain green tea. In one embodiment, the green tea-containing kibbles may be more than about 0.1%, 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In another embodiment, the green tea-containing kibbles may be less than about 0.1%, 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In another diet of food kibbles, only some of the kibbles contain pomegranate. In one embodiment, the pomegranate-containing kibbles may be more than about 0.1%, 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In another embodiment, the pomegranate-containing kibbles may be less than about 0.1%, 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight.

The primarily disc-shaped kibbles containing one or more botanicals may be combined or mixed with food kibbles containing the same or different nutrition components in a diet. For example, the primarily disc-shaped food kibbles containing one or more botanicals are combined or mixed with food kibbles that do not contain botanicals. In some embodiments, the primarily disc-shaped kibbles containing one or more botanicals may be more than about 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In some embodiments, the primarily disc-shaped kibbles containing one or more botanicals may be less than about 1%, 5%, 10%, 15%, 20%, 25%, 30%, 35%, 40%, 45%, 50%, 55%, 60%, 65%, 70%, 75%, 80%, 85%, 90%, 95%, 99% or 100% of the total food kibble by weight. In some embodiments, the food kibbles that do not contain botanicals also have a primarily disc shape.

The primarily disc-shaped kibbles containing one or more botanicals may be combined or mixed with other types of dry food, canned food or wet food. In some embodiments, the primarily disc-shaped kibbles containing one or more botanicals may be more than about 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In some embodiments, the primarily disc-shaped kibbles containing one or more botanicals may be less than about 5%, 10%, 15%, 20%, 25%, 30%, 35%, 40%, 45%, 50%, 55%, 60%, 65%, 70%, 75%, 80%, 85%, 90%, 95%, 99% or 100% of the total food kibble by weight. In some embodiments, the primarily disc-shaped kibbles containing one or more botanicals may be combined or mixed with other types of animal food before being fed to the animal. For example, the primarily disc-shaped kibbles containing one or more botanicals may be combined or mixed with other types of dry food, canned food or wet food. In some embodiments, the primarily disc-shaped kibbles containing one or more botanicals may be more than about 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In some embodiments, the primarily disc-shaped kibbles containing one or more botanicals may be less than about 5%, 10%, 15%, 20%, 25%, 30%, 35%, 40%, 45%, 50%, 55%, 60%, 65%, 70%, 75%, 80%, 85%, 90%, 95%, 99% or 100% of the total food kibble by weight.

The primarily disc-shaped kibbles containing one or more botanicals of the current invention may be combined or mixed with food kibbles with one or more other shapes, such as but not limited to a cylinder, a sphere, a square, a triangle, or a pillow. In some embodiments, the primarily disc-shaped kibbles containing one or more botanicals may be more than about 1%, 5%, 10%, 15%, 20%, 25%, 30%, 35%, 40%, 45%, 50%, 55%, 60%, 65%, 70%, 75%, 80%, 85%, 90%, 95% or 99% of the total food kibble by weight. In some embodiments, the primarily disc-shaped kibbles containing one or more botanicals may be less than about 5%, 10%, 15%, 20%, 25%, 30%, 35%, 40%, 45%, 50%, 55%, 60%, 65%, 70%, 75%, 80%, 85%, 90%, 95%, 99% or 100% of the total food kibble by weight.

The oral inflammation of the animal may be assessed with a graded oral inflammation score. When an animal ingests the primarily disc-shaped food kibbles comprising one or more botanicals, such as but not limited to curcumin, a reduction of oral inflammation is achieved in the animal, as reflected by a reduction of the graded oral inflammation score.

As used herein, the term "reduction" or "reduce" in the context of oral inflammation is used to refer, for example, to a decrease of oral inflammation levels in the same animal over time during which the animal ingests the primarily disc-shaped food kibbles containing one or more botanicals of the present invention compared to a baseline level of oral inflammation in the same animal before the ingestion of the primarily disc-shaped food kibbles, or a decrease of oral inflammation levels in an animal that ingests the primarily disc shaped food kibbles comprising one or more botanicals compared a control (different) animal that ingests control food kibbles. In some embodiments, a reduction of oral inflammation is reflected by a decrease of at least about 5%, 10%, 15%, 20%, 25%, 30%, 40%, 45%, 50%, 55%, 60%, 65%, 70%, 75%, 80%, 85%, 90%, 95% or 100% of the graded oral inflammation score.

As used herein, the term baseline in the context oral inflammation is intended to mean the level of oral inflammation prior to the animal ingesting the primarily disc shaped food kibbles comprising one or more botanicals. The baseline level may be one measurement of the oral inflammation prior to the animal ingesting the primarily disc-shaped food kibbles comprising one or more botanicals. The baseline level may also be an average of a number of measurements of the oral inflammation prior to the animal ingesting the primarily disc-shaped food kibbles comprising one or more botanicals. Therefore, the methods of the present invention may further comprise measuring oral inflammation in the animal prior to the animal ingesting the primarily disc-shaped food kibbles comprising one or more botanicals.

In some embodiments, the methods of the present invention may further comprise measuring oral inflammation in the animal at one or more time points after the animal has ingested the primarily disc-shaped food kibbles comprising one or more botanicals and comparing the measured oral inflammation to the baseline. In some embodiments, ingesting primarily disc shaped food kibbles comprising one or more botanicals achieves a reduction of oral inflammation, as measured by the decrease of oral inflammation compared to the baseline level. In some embodiments, ingesting primarily disc shaped food kibbles comprising one or more botanicals achieves a reduction of the graded oral inflammation score from about 3 to about 2, from about 3 to about 1, from about 3 to about 0, from about 2 to about 1, from about 2 to about 0, or from about 1 to about 0.

In some embodiments, the methods of the present invention may comprise treating oral inflammation in an animal, comprising feeding the animal primarily disc-shaped food kibbles comprising one or more botanicals, wherein a reduction of oral inflammation is achieved in the animal after or during ingestion of the disc-shaped kibbles. The oral inflammation after or during the ingestion of the primarily disc shaped food kibbles in the animal may be compared to a baseline level before the ingestion. In some embodiments, the reduction of oral inflammation is reflected by a decrease of at least about 5%, 10%, 15%, 20%, 25%, 30%, 40%, 45%, 50%, 55%, 60%, 65%, 70%, 75%, 80%, 85%, 90%, 95% or 100% of the graded oral inflammation score compared to baseline levels.

In some embodiments, the methods of the present invention may comprise reducing the likelihood of developing oral inflammation in an animal, comprising feeding the animal primarily disc-shaped food kibbles comprising one or more botanicals, wherein a reduction of the likelihood of developing oral inflammation is achieved in the animal after or during ingestion of the disc-shaped kibbles.

In some embodiments, the animal ingesting the primarily disc-shaped food kibbles containing one or more botanical has a reduction of graded oral inflammation score at least about 5%, 10%, 15%, 20%, 25%, 30%, 35%, 40%, 45%, 50%, 55%, 60%, 65%, 70%, 75%, 80%, 85%, 90%, 95%, 99% or 100% compared to the baseline graded oral inflammation score of the same animal before ingesting the primarily disc-shaped food kibbles containing one or more botanicals.

The reduction of oral inflammation of the animal ingesting the primarily disc shaped food kibbles containing one or more botanicals compared to the baseline graded oral inflammation score of the same animal before ingesting the primarily disc-shaped food kibbles containing one or more botanicals may be observed after the animal has been ingesting the primarily disc-shaped food kibbles containing one or more botanicals for a period of time. In some embodiments, the reduction of oral inflammation is observed after about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, 150 or 200 days after ingesting the primarily disc-shaped food kibbles containing one or more botanicals at least once a day. In one embodiment, the reduction of oral inflammation is observed after about 70 days. In some embodiments, the reduction of oral inflammation is observed in less than about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, 150 or 200 days.

In some embodiments, the animal ingesting the primarily disc-shaped food kibbles containing one or more botanicals has a reduction of graded oral inflammation score at least about 5%, 10%, 15%, 20%, 25%, 30%, 35%, 40%, 45%, 50%, 55%, 60%, 65%, 70%, 75%, 80%, 85%, 90%, 95%, 99% or 100% compared to the graded oral inflammation score of a control animal ingesting control food kibbles. In some embodiments, the animal ingesting the primarily disc-shaped food kibbles containing one or more botanicals and the control animal are cats. In some embodiments, the animal ingesting the primarily disc-shaped food kibbles containing one or more botanicals and the control animal are kittens. In some embodiments, the control food kibbles do not contain botanicals. In some embodiments, the control food kibbles comprise botanicals. In some embodiments, the control food kibbles comprise different botanicals compared to the primarily disc-shaped food kibbles. In some embodiments, the control food kibbles comprise the same botanicals in different percentages compared the primarily disc-shaped food kibbles. In some embodiments, the control food kibbles comprise the same botanicals in same percentages compared the primarily disc-shaped food kibbles. In some embodiments the control food kibbles comprise the same botanicals in same percentages compared to the primarily disc-shaped food kibbles containing one or more botanicals but do not have a disc shape. In some embodiments the control food kibbles comprise different botanicals or in different percentages compared to the primarily disc-shaped food kibbles containing one or more botanicals. In some embodiment, the control kibbles comprise food kibbles that have a disc shape but do not contain botanicals. In some embodiments, the control kibbles comprise food kibbles having a cylindrical shape with a height to diameter ration of about or more than about 1:1. In some embodiments, the control kibbles comprise food kibbles having a cylindrical shape with a height to diameter ration of about or more than about 1:1 and being supplemented with one or more botanicals.

The reduction of oral inflammation in the animal ingesting the primarily disc-shaped food kibbles compared to the control animals may be observed after the animals have been ingesting the primarily disc-shaped food kibbles for a period of time. In some embodiments, the reduction of oral inflammation is observed after about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, 150 or 200 days. In one embodiment, the reduction of oral inflammation is observed after about 70 days after ingesting the primarily disc-shaped food kibbles containing one or more botanicals at least once a day.

In some embodiments, the graded oral inflammation score of the animal is at least 20% lower than the graded oral inflammation score of a control animal ingesting control food kibbles, wherein the control food kibbles have a disc shape but do not contain botanicals.

In some embodiments, the graded oral inflammation score of the animal is at least 80% lower than the graded oral inflammation score of a control animal ingesting control food kibbles, wherein the control food kibbles do not have a disc shape but contain botanicals. In some embodiments, the control food kibbles may have a cylindrical shape with a height to diameter ration of about or more than about 1:1 and be supplemented with botanicals, such as but not limited to curcumin.

The current invention also relates to methods of making a food kibble comprising one or more botanicals, wherein the food kibble has primarily a disc shape and reduces oral inflammation in an animal when the animal ingests the food kibble.

The current invention also relates to a method for making food kibbles containing one or more botanicals, the method comprising (a) preconditioning by mixing wet and dry ingredients at elevated temperature to form a kibble dough, (b) extruding the kibble dough at a high temperature and pressure through an extruder configured to form food kibbles having primarily a disc shape, (c) drying the extruded disc-shaped food kibbles, and (d) enrobing the dried disc-shaped food kibbles with topical liquid and/or dry ingredients, wherein the one or more botanicals are applied at (a) and/or (d) in an amount effective to reduce oral inflammation in an animal when the animal ingests the food kibbles.

The kibble dough can be prepared in any suitable means from any suitable ingredients, such as, for example, a protein source, a carbohydrate source, a fat source, and any other ingredients suitable for animal or pet nutrition.

Similarly, the topical liquid and/or dry ingredients that are used to enrobing the food kibbles can be prepared in any suitable means from any suitable ingredients, such as, for example, a protein source, a carbohydrate source, a fat source, and any other ingredients suitable for animal or pet nutrition.

In some embodiments, the food kibbles of the present invention comprise one or more ingredients such as but not limited to flax, corn, rim brewers, pea, chicken, soybean, tomato, cellulose, wheat, beet, lysine, potassium chloride, methionine, sodium chloride, carrot, dicalcium phosphate, vitamin premix, carnitine lipoic acid alpha, mineral premix, calcium carbonate, taurine, glucosamine hydrochloride, chondroitin sulfate, grain blend, lactic acid, choline chloride, grain blend, palatant, fish oil, coconut oil, vitamin E oil, starch, poultry, fish, dairy, pork, beef, lamb, venison, and rabbit.

In some embodiments, the food kibbles of the present invention comprise one or more amino acid such as but not limited to arginine, histidine, isoleucine, leucine, lysine, methionine, phenylala nine, threonine, tryptophan, valine, taurine, carnitine, alanine, aspartate, cystine, glutamate, glutamine, glycine, proline, serine, tyrosine, and hydroxyproline.

In some embodiments, the food kibbles of the present invention comprise one or more fatty acids such as but not limited to lauric acid, myristic acid, palmitic acid, palmitoleic acid, margaric acid, margaroleic acid, stearic acid, oleic acid, linoleic acid, g-linolenic acid, a-linolenic acid, stearidonic, arachidic acid, gadoleic acid, DHGLA, arachidonic acid, eicossatetra acid, EPA, behenic acid, erucic acid, docosatetra acid, and DPA.

In some embodiments, the food kibbles of the present invention comprise one or more macro nutrients such as but not limited to moisture, protein, fat, crude fiber, ash, dietary fiber, soluble fiber, insoluble fiber, raffinose, and stachyose.

In some embodiments, the food kibbles of the present invention comprise one or more micro nutrients such as but not limited to beta-carotene, alpha-lipoic acid, glucosamine, chondroitin sulfate, lycopene, lutein, and quercetin.

In some embodiments, the food kibbles of the present invention comprise one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food kibbles of the present invention comprise one or more vitamins such as but not limited to vitamin A, vitamin D, vitamin E, vitamin K, vitamin C, thiamine, riboflavin, niacin, pyridoxine, pantothenic acid, folic acid, vitamin B12, biotin, choline

EXAMPLES

Example 1

Standard palatability measurement system was used to assess the effects of kibble shape on the palatability of food kibbles. In this study, kibble intake was evaluated by analyze the ratio of the intake of the food kibble in question in comparison to a competitive control. In this experimental calculation of the ratio is as follows: the amount of test food consumed (example disc shape below) intake divided by the total intake of foods offered. Results are shown in Table 1.

TABLE 1

Assessment of food kibble intake

| Shape | Ratio LSMEAN | Standard Error | LSMEAN Pr |
|---|---|---|---|
| Disc | 0.51043443 | 0.02203138 | <0.0001 |
| Pillow | 0.50992424 | 0.02203138 | <0.0001 |
| Triangle | 0.48416794 | 0.02184342 | <0.0001 |

In Table 1, LSMEAN refer to least squares means. The data show that the preferred shape for taste is the disc shape.

Example 2

The effects of kibble shape and botanicals were assessed by feeding cats with food kibbles having different shapes and with or without botanical supplementation. The cats were ingesting the food kibbles for 10 weeks. Oral inflammation was assessed by a single qualified dental technician who was blinded to the study. Graded oral inflammation scores were generated by measuring symptoms of oral inflammation, such as redness and swelling, based on a score system of 0=None, 1=Mild, 2=Moderate, to 3=Severe. The final score reflects oral inflammation of the gums and the entire mouth of each animal. The results are shown in Table 2.

TABLE 2

| Food Kibbles | % Change (Oral Inflammation Score) | Standard Error | LS-Means Pr |
|---|---|---|---|
| Control | 0.10314750 | 0.09830202 | 0.3060 |
| Control + curcumin | 0.48891807 | 0.09871192 | <0.0001 |
| Disc | −0.02539105 | 0.10497618 | 0.8112 |
| Disc + all | −0.23757072 | 0.10565098 | 0.0354 |
| Disc + curcumin | −0.28070930 | 0.10497618 | 0.0142 |

In Table 2, "Control" refers to the groups fed with food kibbles having a cylindrical shape with a height to diameter ratio of about 1:1; "Disc" refers to the groups fed with food kibbles having a disc shape as detailed herein; "all" refers to a combination of botanicals curcumin, green tea and pomegranate. The amount of curcumin in "Control+curcumin" and "Disc+curcumin" samples is about 0.1% of the total food kibble by weight. The amount of all three botanicals in "Disc+all" sample is about 0.1% of the total food kibble by weight.

Table 2 shows as percent change (as a ratio) in all foods compared to what it would be with no intervention. The disc shape was shown to have a unique and unexpected benefit in that in comparison to control cat food. The addition of the botanicals resulted in an improvement in oral inflammation scores (over 20% reduction) in comparison to control food with curcumin, where there was a significant worsening of inflammation scores (over 40% increase).

There is a significant interaction of shape and botanicals (P=0.0082) in that there is an improvement in the disc shape with added curcumin (P=0.0142) or when curcumin was added with green tea and pomegranate in the disc-shaped food kibbles (p=0.0354) while there is an increase in oral inflammation when curcumin was added to the control cat food.

What is claimed is:

1. A method of reducing or treating oral inflammation in an animal, comprising feeding the animal a pet food composition comprising a plurality of primarily disc-shaped food kibbles,
    wherein the primarily disc-shaped food kibbles comprise a top circular surface having a diameter substantially equal to a diameter of a bottom circular surface and have a thickness to diameter ratio of from about 1:5 to about 1:15,
    wherein the primarily disc-shaped food kibbles comprise one or more botanicals comprising curcumin, wherein the botanicals are present in an amount of from about 0.1 weight % to about 0.5 weight %, based on a total weight of the plurality of food kibbles, and
    wherein a reduction of oral inflammation is achieved in the animal after or during ingestion of the disc-shaped kibbles.

2. The method of claim 1, wherein the animal is a cat or a kitten.

3. The method of claim 1, wherein the one or more botanicals is one botanical consisting of curcumin.

4. The method of claim 1, wherein the one or more botanicals further comprises at least one of green tea and pomegranate.

5. The method of claim 1, wherein the oral inflammation in the animal is reduced after the animal ingests the primarily disc-shaped food kibbles for about 70 days.

6. The method of claim 1, further comprising measuring oral inflammation in the animal prior to the animal ingesting the primarily disc-shaped food kibbles comprising one or more botanicals and establishing a baseline oral inflammation.

7. The method of claim 6, further comprising measuring oral inflammation in the animal at one or more time points after the animal has ingested the primarily disc-shaped food kibbles comprising one or more botanicals and comparing the measured oral inflammation to the baseline oral inflammation.

8. The method of claim 7, wherein oral inflammation is measured by a graded oral inflammation score and the graded oral inflammation score of the animal after the animal ingests the primarily disc-shaped food kibbles comprising one or more botanicals is at least 20%, 40%, 60%, 80% or 90% lower than the graded oral inflammation score of the baseline oral inflammation.

9. The method of claim 7, wherein the time point is least about 70 days after the animal ingests the primarily disc-shaped food kibbles comprising one or more botanicals.

10. The method of claim 7, wherein oral inflammation is measured by a graded oral inflammation score and the graded oral inflammation score of the animal ingesting the primarily disc-shaped food kibbles comprising one or more botanicals is at least 20%, 40%, 60%, 80% or 90% lower than the graded oral inflammation score of a control animal that ingests control food kibbles, wherein the control food kibbles do not have a disc shape.

11. The method of claim 10, wherein the primarily disc-shaped food kibbles have improved palatability compared to the control food kibbles.

12. The method of claim 1, wherein the one or more botanicals comprises curcumin in an amount of about 0.1 weight %, based on a total weight of the plurality of food kibbles.

13. The method of claim 1, wherein the primarily disc shape has a thickness to diameter ratio of from about 1:10 to about 1:15.

14. The method of claim 1, wherein the pet food composition further comprises wet food, wherein the wet food is combined with the plurality of primarily disc-shaped food kibbles.

15. The method of claim 1, wherein the primarily disc-shaped food kibbles have a thickness of less than about 5 mm.

16. The method of claim 1, wherein the primarily disc-shaped food kibbles have a thickness of less than about 4 mm.

17. The method of claim 1, wherein the primarily disc-shaped food kibbles have a thickness of less than about 3 mm.

18. The method of claim 1, wherein the primarily disc-shaped food kibbles have a thickness of less than about 2 mm.

19. The method of claim 1, wherein the primarily disc-shaped food kibbles have a thickness of from about 1 mm to about 2 mm.

\* \* \* \* \*